United States Patent
Brandolini et al.

(10) Patent No.: US 12,268,671 B2
(45) Date of Patent: Apr. 8, 2025

(54) IL-8 INHIBITORS FOR USE IN THE TREATMENT OF CHEMOTHERAPY-INDUCED PERIPHERAL NEUROPATHY

(71) Applicant: DOMPÉ FARMACEUTICI S.P.A., Milan (IT)

(72) Inventors: Laura Brandolini, L'Aquila (IT); Pier Adelchi Ruffini, Milan (IT); Marcello Allegretti, Rome (IT)

(73) Assignee: DOMPÉ FARMACEUTICI S.P.A., Milan (IT)

( * ) Notice: Subject to any disclaimer, the term of this patent is extended or adjusted under 35 U.S.C. 154(b) by 209 days.

(21) Appl. No.: 16/066,072

(22) PCT Filed: Jan. 13, 2017

(86) PCT No.: PCT/EP2017/050637
§ 371 (c)(1),
(2) Date: Jun. 26, 2018

(87) PCT Pub. No.: WO2017/121838
PCT Pub. Date: Jul. 20, 2017

(65) Prior Publication Data
US 2019/0015391 A1   Jan. 17, 2019

(30) Foreign Application Priority Data

Jan. 15, 2016 (EP) ..................................... 16151618
Sep. 27, 2016 (EP) ..................................... 16190871

(51) Int. Cl.
| | | |
|---|---|---|
| A61K 31/165 | (2006.01) | |
| A61K 31/18 | (2006.01) | |
| A61K 31/19 | (2006.01) | |
| A61K 31/192 | (2006.01) | |
| A61K 31/426 | (2006.01) | |
| A61P 25/00 | (2006.01) | |
| A61P 25/02 | (2006.01) | |
| A61P 27/02 | (2006.01) | |

(52) U.S. Cl.
CPC .......... *A61K 31/426* (2013.01); *A61K 31/165* (2013.01); *A61K 31/19* (2013.01); *A61K 31/192* (2013.01); *A61P 25/02* (2018.01)

(58) Field of Classification Search
CPC .... A61K 31/165; A61K 31/192; A61K 31/19; A61K 31/18; A61P 25/02; A61P 25/00; A61P 27/02
USPC ....................................................... 514/605
See application file for complete search history.

(56) References Cited

FOREIGN PATENT DOCUMENTS

| | | | |
|---|---|---|---|
| WO | WO2000024710 | 5/2000 | |
| WO | WO2005090295 | 9/2005 | |
| WO | WO2008039876 | 4/2006 | |
| WO | WO-2008039876 A1 * | 4/2008 | ............. A61K 31/00 |
| WO | WO2010031835 | 3/2010 | |
| WO | WO2016016178 | 2/2016 | |

OTHER PUBLICATIONS

Polomano, R., A. Mannes, U. Clark and G. Bennett "A painful peripheral neuropathy in the rat produced by the chemotherapeutic drug, paclitaxel" Pain (2001), 94; pp. 293-304. (Year: 2001).*
Quasthoff, S. and H. Hartung, "Chemotherapy-induced peripheral neuropathy", J Neurol (2002), 249: pp. 9-17. (Year: 2002).*
Kim, et al., Spine, Dec. 1, 2011, vol. 31, No. 25, 2139-2146.
Argyriou, Andreas, A., et al., "Chemotherapy-induced peripheral neuropathy in adults: a comprehensive update of the literature", Cancer Management and Research, 6. 2014, pp. 135-147.
Argyriou, Andreas, A., et al., "Chemotherapy-induced peripheral neurotoxicity (CIPN): An update", Critical Reviews in Oncology/Hematology, 82, 2012, pp. 51-77.
Bertini, R.. et al., "Receptor binding mode and pharmacological characterization of a potent and selective dual CXCR1/CXCR2 non-competitive allosteric inhibitor", British Journal of Pharmacology, 165, 2012, pp. 436-454.
BErtini, Riccardo, et al., "Noncompetitive allosteric inhibitors of the inflammatory chemokine receptors CXCR1 and CXCR2: Prevention of reperfusion injury", PNAS, vol. 101, No. 32, Aug. 10, 2004, pp 11791-11796.
Boyette-Davis, J., et al., "Intraepidermal nerve fiber loss corresponds to the development of Taxol-induced hyperalgesia and can be prevented by treatment with minocycline"; Pain, 152(2), Feb. 2011, pp. 308-313.
Brewer, Jamie. R., et al., "Chemotherapy-induced peripheral neuropathy: Current status and progress", Gynecologic Oncology, 140, 2016, pp. 176-183.
Cavaletti, G., et al., "Effects of different schedules of oxaliplatin treatment on the peripheral nervous system of the rat", European Journal of Cancer, 37, 2001, pp. 2457-2463.
Cavalieri, B., et al., "Neutrophil recruitment in the reperfused-injured rat liver was effectively attenuated by repertaxin, a novel allosteric non-competitive inhibitor of CXCL8 receptors: A therapeutic approach for the treatment of post-ischemic hepatic syndromes", International Journal of Immunopathology and Pharmacology, vol. 18, No. 3, 2005, pp. 475-486.
Depaola, Massimiliano, et al., "Chemokine MIP-2/CXCL2, acting on CXCR2, induces motor neuron death in primary cultures", Neuroimmunomodulation. 14, 2007. pp 310-316.
EESR from EP16151618.2 dated Jun. 3, 2016.

(Continued)

Primary Examiner — Samantha L Shterengarts
Assistant Examiner — Sagar Patel
(74) Attorney, Agent, or Firm — HUESCHEN AND SAGE

(57) ABSTRACT

The present invention relates to IL-8 inhibitor compounds, preferably dual CXCR1/CXCR2 receptor inhibitors, useful in the treatment and/or prevention of chemotherapy-induced neuropathy, preferably in the treatment and/or prevention of chemotherapy-induced peripheral neuropathy (CIPN) or chemotherapy-induced optic neuropathy.

16 Claims, 4 Drawing Sheets

(56) References Cited

OTHER PUBLICATIONS

Fincham, N J, et al., "Neutrophil chemoattractant and IL-1-like activity in samples from psoriatic skin lesions. Further characterization", J. Immunol., 140, 1988, pp. 4294-4299.

Griffin, Thomas, D., et al., "Clinical and histologic heterogeneity of psoriatic plaques", Arch Dermatol. vol. 124, Feb. 1988, pp. 216-220.

International Search Report for PCT/EP2017/050637 dated Mar. 8, 2017.

Jeffery, Peter. K., "Structural and inflammatory changes in COPD: a comparison with asthma", Thorax, 53, 1998, pp. 129-136.

Lapointe, Nichole, E., et al., "Effects of eribulin, vincristine, paclitaxel and ixabepilone on fast axonal transport and kinesin-1 driven microtubule gliding: Implications for chemotherapy-induced peripheral neuropathy", Neurotoxicology, 37, Jul. 2013, pp. 231-239.

Lefer, Allan, M., et al., "Cardioprotective and endothelial protective effects of [Ala-IL8]77 in a rabbit model of myocardial ischaemia and reperfusion", Br. J. Pharamacol. 103, 1991, pp. 1153-1159.

Liu, Zhi, et al., "A major role for neutrophils in experimental bullous pemphigoid", The Journal of Clinical Investigations, vol. 100., No. 5, Sep. 1997, pp. 1256-1263.

Lopes, Alexandre, H., et al., "DF2755A, a novel non-competitve allosteric inhibitor of CXCR1/2. reduces inflammatory and post-operative pain", Pharmacological Research, 103. 2016, pp. 69-79.

Mielke, Stephan, et al., "Peripheral neuropathy: A persisting challenge in paclitaxel-based regimes", European Journal of Cancer, 42, 2006. pp. 24-30.

Moriconi, Alessio, et al., PNAS, vol. 111, No. 47, Nov. 25, 2014, pp. 16937-16942 and Correction in PNAS, vol. 111, No. 52, Dec. 30, 2014, pp. 18799.

Pachman, DR, et al., "Chemotherapy-induced peripheral neuropathy: prevention and treatment", Clinical Pharmacology & Therapeutics, vol. 90, No. 3, Sep. 2011, pp. 377-387.

Pesci, A., et al., "Inflammatory cells and mediators in bronchial lavage of patients with chronic obstructive pulmonary disease", Eur. Respir. J. 12, 1998, pp. 380-386.

Polomano, Rosemary, C., et al., "A painful peripheral neuropathy in the rat produced by the chemotherapeutic drug, paclitaxel", Pain, 94, 2001, pp. 293-304.

Ramesh, Geeta, "Novel therapeutic targets in neuroinflammation and neuropathic pain", Inflamm Cell Signal, 1(3), 2014.

Romson, Joseph, L., et al., "Reduction of the extent of ischemic myocardial injury by neutrophil depletion in the dog", Circulation 67, No. 5, 1983, pp. 1016-1023.

Sekido, Nobuaki, et al., "Prevention of lung reperfusion injury in rabbits by a monocolonal antibody against interleukin-8", Nature, vol. 365, Oct. 14, 1993, pp. 654-657.

Takematsu, Hideaki, et al., "Quantification of chemotactic peptides (C5a anaphylatoxin and IL-8) in psoriatic lesional skin", Arch Dermatol, vol. 129, Jan. 1993, pp. 74-80.

Wang, Xiao-Min, et al., "Discovering cytokines as targets for chemotherapy-induced painful peripheral neuropathy", Cytokine, 59(1), Jul. 2012, pp. 3-9.

Welbourn. C. R. B., et al., "Pathophysiology of ischaemia reperfusion injury: central role of the neutrophil", Br. J. Surg., vol. 78, Jun. 1991, pp. 651-655.

Windebank, Anthony, J., et al., "Chemotherapy-induced neuropathy", Journal of the Peripheral Nervous System, 13, 2008, pp. 27-46.

Wolf, Marlene, et al., "Granulocyte chemotactic protein 2 acts via both IL-8 receptors, CXCR1 and CXCR2", Eur. J. Immunol., 28, 1998, pp. 164-170.

Duncan, et al., Experimental Neurology, 2016, 283, 452-475.

Hou, et al., Pain Physician, 2018, 21, 571-592.

Wikipedia entry for Demyelinating disease (https://en.wikipedia.org/wiki/Demyelinating_disease).

Gilardini, et al., Neurotoxicology, 2012, 33, 1-7.

Love, J. Clin. Pathol., 2006, 59, 1151-1159.

\* cited by examiner

IL-8 INHIBITORS FOR USE IN THE TREATMENT OF CHEMOTHERAPY-INDUCED PERIPHERAL NEUROPATHY

TECHNICAL FIELD

The present invention relates to IL-8 inhibitors for the prevention and treatment of chemotherapy-induced peripheral neuropathy (CIPN) and in particular of allodynia associated thereof.

BACKGROUND ART

Chemotherapy is often associated with neurotoxic side effects, which constitute major dose limiting factors for this treatment. In particular, chemotherapy has been reported to cause both peripheral neuropathy as well as ocular complications, such as optic neuropathy.

"Chemotherapy-induced peripheral neuropathy (CIPN)" indicates a dose-limiting neurotoxic effect of chemotherapy to peripheral nerves. A number of different symptoms are associated with CIPN: hyperalgesia, allodynia, and spontaneous sensations such as burning, pain, numbness, spasm, and itching. In particular, although some of the symptoms induced by neurotoxicity of chemotherapeutic agents differs from patient to patient, a common sensory disruption leading to painful paresthesia is common to all affected patients.

CIPN occurs in about 60% of cancer patients (Windebank et al, J Peripher Nerv Syst 2008; 13:27-46) and can lead to dose limitation or even discontinuation of treatment, therefore ultimately affecting survival of the patient (Mielke et al, Eur J Cancer 2006; 42:24-30).

The broad spectrum of ophthalmic complications induced by cytotoxic chemotherapy includes reversible and irreversible acute and chronic disorders. Mild to moderate ophthalmic complications are very common and reversible after cessation of anti-cancer therapy. Some major ocular toxicities may require a dose reduction or the discontinuation of cytotoxic chemotherapy in order to prevent visual loss. Among the ocular complications, chemotherapy-induced optic neuropathy has been reported in association with elevated intracranial pressure due to anterior ischemic optic neuropathy related to the use of some chemotherapeutic agents.

In particular, the chemotherapeutic agents that are most commonly associated with the onset of neuropathy include platinum-based drugs, for example cisplatin, carboplatin and oxaliplatin; taxanes, for example paclitaxel, cabazitaxel and docetaxel; epothilones, for example ixabepilone; plant alkaloids, for example vinblastine, vincristine, vinorelbine and etoposide; thalidomide, lenalidomide and pomalidomide; carfilzomib and bortezomib; eribulin (Brewer et al, Gynecologic Oncology 2016; 140:176-83).

Although a variety of neuroprotective approaches have been investigated in both experimental studies and clinical trials, there is at the moment no available preventive strategy or effective treatment for CIPN or chemotherapy-induced optic neuropathy, also because their etiology have not yet been fully elucidated.

Multiple mechanisms have been proposed to underlie the development and maintenance of neuropathy.

Some evidence suggests that inflammatory cytokines/chemokines and in particular TNF-$\alpha$, IL-$\beta$, IL-6 and CCL2 may have a role in chemotherapeutic agent-induced pain symptoms in CIPN (Wang et al, Cytokine 2012; 59 (1): 3-9). However, strong evidence also suggests a direct effect of chemotherapeutic drugs on sensory neurons (Argyriou et al, Crit Rev Onol Hematol 2012, 82 (1) 51-77, Boyette-Davis et al, Pain, 2011; 152:308-13; Pachman et al, Clin Pharmacol Ther 2011; 90:377-387). In particular, it has been established that most chemotherapeutic drugs can easily penetrate the blood-nerve-barrier (BNB) and bind to the dorsal root ganglia (DRG) and peripheral axons (Wang et al, see above). There is also evidence that these drugs then directly damage the structure of the DRG cells and peripheral nerves with the consequent degeneration of sensory fibers and loss of small nerve fibers in the epidermal layer (Argyriou et al, Cancer Manag Res. 2014; 6:135-147).

At the cellular level neurotoxic chemotherapeutic agents damage microtubules, interfere with microtubule-based axonal transport (LaPointe et al, Neurotoxicology 2013; 37:231-9), affect microtubule dynamics, by inducing $\alpha$-tubulin acetylation, interrupt mitochondrial function, or directly target DNA. Nerve biopsies from experimental animals and patients treated with paclitaxel, oxaliplatin or vincristine show identical morphological changes, suggesting an underlying common pathogenetic mechanism.

Interleukin-8 (IL-8; CXCL8) is considered major mediator of PMN (Polymorphonuclear Neutrophils) recruitment and is involve in several pathologies including psoriasis, rheumatoid arthritis, chronic obstructive pulmonary disease and reperfusion injury in transplanted organ (Griffin et al, Arch Dermatol 1988, 124:216; Fincham et al, J Immunol 1988, 140:4294; Takematsu et al, Arch Dermatol 1993, 129:74; Liu et al, 1997, 100:1256; Jeffery, Thorax 1998, 53:129; Pesci et al, Eur Respir J. 1998, 12:380; Lafer et al, Br J Pharmacol. 1991, 103:1153; Romson et al, Circulation 1993, 67:1016; VVelbourn et al, Br J Surg. 1991, 78:651; Sekido et al, Nature 1993, 365, 654). The biological activity of IL-8 is mediated by the interaction with two receptors, CXCR1 and CXCR2, belonging to the 7TM-GPCR family, that are expressed on the surface of human PMNs. While CXCR1 is selective, binding with high affinity only two chemokines, CXCL6 and IL-8, and showing a much higher affinity for IL-8 (Wolf et al. Eur J Immunol 1998, 28:164), human CXCR2 is a more promiscuous receptor, binding a number of different cytokines and chemokines. Therefore, CXCR2 mediates the activity of a number of different biological molecules.

SUMMARY OF THE INVENTION

The present inventors have surprisingly found that inhibition of IL-8 is able to reduce or prevent the occurrence of symptoms associated with toxicity of systemic anticancer chemotherapy leading to chemotherapy-induced peripheral neuropathy (CIPN) and chemotherapy-induced optic neuropathy.

Accordingly, a first object of the present invention is an IL-8 inhibitor, preferably an antibody or a small molecular weight molecule, preferably a CXCR1 inhibitor, more preferably a dual CXCR1/CXCR2 inhibitor, for use in the prevention and/or treatment of chemotherapy-induced neuropathies. The second object of the present invention is the use of said IL-8 inhibitor as defined above, for the preparation of a medicament for the prevention and/or treatment of CIPN or chemotherapy-induced optic neuropathy.

The third object of the present invention is a method for the prevention and/or treatment of CIPN and chemotherapy-induced optic neuropathy comprising the step of administering to a subject in need thereof a therapeutically effective amount of said IL-8 inhibitor.

The fourth object of the invention is a pharmaceutical composition for the prevention and/or treatment of CIPN and chemotherapy-induced optic neuropathy comprising an IL-8 inhibitor according to the invention and pharmaceutically acceptable excipients and/or diluents.

DETAILED DESCRIPTION OF THE INVENTION

Figure 1:
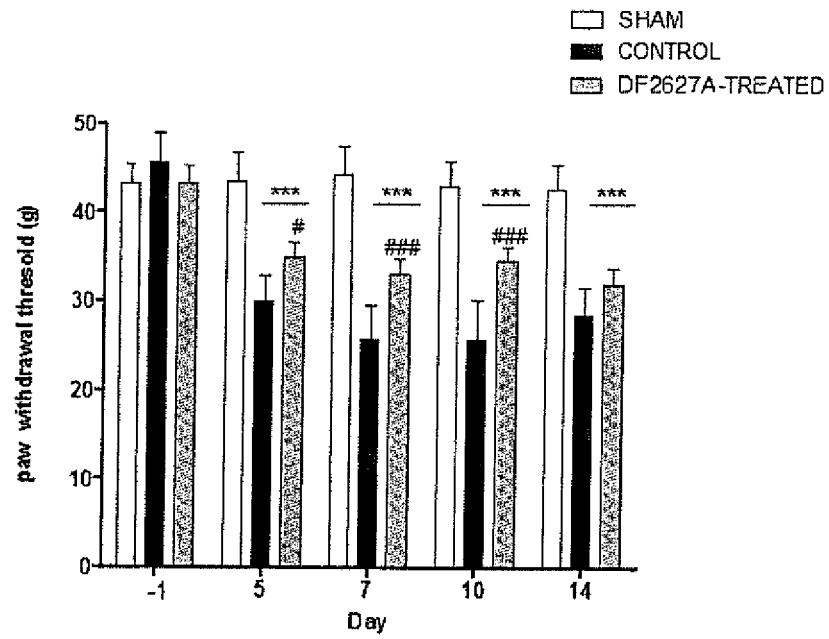
FIG. 1 represents the paw withdrawal threshold, indicating the induction of allodynia by mechanical stimuli, measured as grams (g), in animals not subjected to any treatment with paclitaxel and/or vehicle/drug (Sham), treated with paclitaxel and vehicle (Control) or with paclitaxel and DF2726A (DF2726A-TREATED), before (day-1), or after (days 5, 7, 10, 14) paclitaxel administration in Control and DF2726A groups. Data are shown as mean±SEM of 10 animals per group. *** represents P<0.001 vs sham group; ### represents P<0.001 and # represents P<0.05 vs Control group.

As it will be disclosed in details in the Experimental Section, the present inventors have found that molecules acting as inhibitors of IL-8 activity have therapeutic efficacy in animal models of neuropathic pain-induced by different chemotherapeutic agents. Furthermore, the present inventors have also found that IL-8 inhibition is able to counteract the activity of chemotherapeutic agents on the cytoskeleton components and organization that contributes to their neurotoxic effects.

Accordingly, a first object of the present invention is an IL-8 inhibitor for use in the treatment and/or prevention of chemotherapy-induced neuropathies.

Preferably, said IL-8 inhibitor is for use in the prevention and/or treatment of chemotherapy-induced peripheral neuropathy (CIPN) or chemotherapy-induced optic neuropathy.

According to a more preferred embodiment, said IL-8 inhibitor is for: use in the prevention and/or treatment of allodynia associated to CIPN.

According to a further preferred embodiment, said IL-8 inhibitor is for use in the prevention and/or treatment of optic pain associated to optic neuropathy.

The term "IL-8-inhibitor" according to the present application refers to any compound able to inhibit, partially or totally, the biological activity of IL-8. Such a compound can act by decreasing the expression or activity of IL-8 or by inhibiting the triggering of the intracellular signaling activated by the IL-8 receptors. It is preferred that said IL-8 inhibitor is able to inhibit at least 50%, preferably at least 60%, of the chemotaxis induced by IL-8 in PMNs at a concentration equal or below 500 nM, preferably below 100 nM.

The second object of the present invention is the use of an IL-8 inhibitor for the preparation of a medicament for the treatment and/or prevention of chemotherapy-induced neuropathies.

Preferably, said IL-8 inhibitor is for use in the prevention and/or treatment of chemotherapy-induced peripheral neuropathy (CIPN) or chemotherapy-induced optic neuropathy.

According to a preferred embodiment of the present invention, said medicament is for the treatment and/or prevention of allodynia associated to chemotherapy-induced peripheral neuropathy.

According to a further preferred embodiment, said IL-8 inhibitor is for use in the prevention and/or treatment of optic pain associated to optic neuropathy.

The third object of the present invention is a method for the treatment and/or prevention of chemotherapy-induced neuropathy, comprising the step of administering to the subject in need thereof, a therapeutically effective amount of an IL-8 inhibitor, as defined above.

Preferably, said method is for the prevention and/or treatment of chemotherapy-induced peripheral neuropathy (CIPN) or chemotherapy-induced optic neuropathy.

According to a preferred embodiment of the present invention, said method is for the treatment and/or prevention of allodynia associated to chemotherapy-induced peripheral neuropathy.

According to a further preferred embodiment, said method is for the treatment and/or prevention of optic pain associated to optic neuropathy.

As used herein, a "therapeutically effective amount" refers to an amount sufficient to achieve treatment or prevention of the disease. Determination of the effective amounts is well within the capability of those skilled in the art based upon the achievement of a desired, effect. An effective amount will depend on factors including, but not limited to, the weight of a subject and/or the degree of the disease or unwanted condition from which a subject suffers. The terms "treatment" and "prevention" as used herein refer to the eradication/amelioration or prevention/delay in onset, respectively, of the disorder being treated or of one or more of the symptoms associated thereof, notwithstanding the fact that the patient may still be afflicted with the underlying disorder.

The fourth object of the present invention is a pharmaceutical composition comprising an IL-8 inhibitor, for use in the treatment and/or prevention of chemotherapy-induced neuropathies in association with pharmaceutically suitable excipients.

Preferably, sad pharmaceutical composition is for the prevention and/or treatment of chemotherapy-induced peripheral neuropathy (CIPN) or chemotherapy-induced optic neuropathy.

According to a preferred embodiment of the present invention, said pharmaceutical composition is for the treatment and/or prevention of allodynia associated to chemotherapy-induced peripheral neuropathy.

According to a further preferred embodiment, said composition is for the use in the prevention and/or treatment of optic pain associated to optic neuropathy.

According to a preferred embodiment, the IL-8 inhibitor of all the objects of the present invention inhibits the activity of IL-8 mediated by CXCR1 receptor or mediated by both CXCR1 and CXCR2 receptors.

Preferably, according to this embodiment, said IL-8 inhibitor is either an allosteric inhibitor or an orthosteric antagonist of CXCR1 receptor or of both CXCR1 and CXCR2 receptors.

Preferably, said IL-8 inhibitor is selective for CXCR1 receptor or is equally potent towards CXCR1 and CXCR2 receptors.

By "selective for CXCR1" according to the present invention it is meant a compound that shows an $IC_{50}$ value at least 2, preferably 3, logs higher toward CXCR1 than towards CXCR2. (Bertini R. et al., Proc. Nat. Acad. Sci USA (2004), 101 (32), pp. 11791-11796).

By "equally potent towards CXCR1 and CXCR2" it is meant a compound that shows an $IC_{50}$ value in the range 10 picomolar ($10^{-11}$M)–1 micromolar ($10^{-6}$M) towards CXCR1 and CXCR2. (Bertini R. et al., Br. J. Pharm. (2012), 165, pp. 436-454).

More preferably, the IL-8 inhibitor according to the invention has an $IC_{50}$ value towards CXCR1 receptor in the low nanomolar range, preferably in the range 0.02-5 nanomolar.

According to a preferred embodiment, also in combination with the preceding embodiment, said IL-8 inhibitor is selected from small molecular weight molecules and antibodies, more preferably it is a small molecular weight molecule.

IL-8 inhibitors according to the above definition, able to inhibit the activity of IL-8 mediated by CXCR1 receptor or mediated by both CXCR1 and CXCR2 receptors, are known in the art.

Preferred IL-8 inhibitors according to the invention are selected from 1,3-thiazol-2-ylaminophenylpropionic acid derivatives, 2-phenyl-propionic acid derivatives and their pharmaceutically acceptable salts.

Among the above compounds, said 1,3-thiazol-2-ylaminophenylpropionic acid derivative is preferably a compound of formula (I):

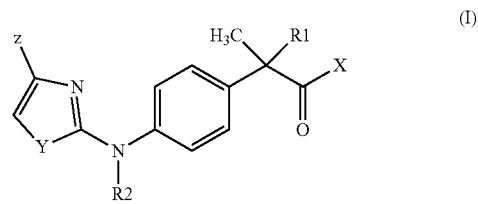

or a pharmaceutically acceptable salt thereof, wherein

R1 is hydrogen or $CH_3$;

R2 is hydrogen or linear $C_1$-$C_4$ alkyl, preferably it is hydrogen;

Y is a heteroatom selected from S, O and N; preferably it is S;

Z is selected from halogen, linear or branched $C_1$-$C_4$ alkyl, $C_2$-$C_4$ alkenyl, $C_2$-$C_4$ alkynyl, $C_1$-$C_4$ alkoxy, hydroxyl, carboxyl, $C_1$-$C_4$ acyloxy, phenoxy, cyano, nitro, amino, $C_1$-$C_4$ acylamino, halo $C_1$-$C_3$ alkyl, halo $C_1$-$C_3$ alkoxy, benzoyl, linear or branched $C_1$-$C_8$ alkanesulfonate, linear or branched $C_1$-$C_8$ alkanesulfonamide, linear or branched $C_1$-$C_8$ alkylsulfonylmethyl; preferably it is trifluoromethyl;

X is OH or a residue of formula $NHR_3$; wherein $R_3$ is selected from:

hydrogen, hydroxyl, linear or branched $C_1$-$C_6$ alkyl, $C_3$-$C_6$ cycloalkyl, $C_2$-$C_6$ alkenyl, $C_1$-$C_5$ alkoxy, or $C_1$-$C_6$ phenylalkyl, wherein alkyl, cycloalkyl or alkenyl group can be substituted by a COOH residue a residue of formula $SO_2R4$ wherein R4 is $C_1$-$C_2$ alkyl, $C_3$-$C_6$ cycloalkyl, $C_1$-$C_3$ haloalkyl.

Preferably, in the above compounds X is OH.

Among the above compounds, particularly preferred are compounds of said formula (I) or pharmaceutically acceptable salts thereof, wherein:

R1 is $CH_3$;

R2 is hydrogen or linear $C_1$-$C_4$ alkyl, preferably it is hydrogen;

Y is a heteroatom selected from S, O and N; preferably it is S;

Z is selected from halogen, linear or branched $C_1$-$C_4$ alkyl, $C_2$-$C_4$ alkenyl, $C_2$-$C_4$ alkynyl, $C_1$-$C_4$ alkoxy, hydroxyl, carboxyl, $C_1$-$C_4$ acyloxy, phenoxy, cyano, nitro, amino, $C_1$-$C_4$ acylamino, halo $C_1$-$C_3$ alkyl, halo $C_1$-$C_3$ alkoxy, benzoyl, linear or branched $C_1$-$C_8$ alkanesulfonate, linear or branched $C_1$-$C_8$ alkanesulfonamides, linear or branched $C_1$-$C_3$ alkytsulfonylmethyl; preferably it is trifluoromethyl;

X is OH or a residue of formula $NHR_3$; wherein $R_3$ is selected from:

hydrogen, hydroxyl, linear or branched $C_1$-$C_6$ alkyl, $C_3$-$C_6$ cycloalkyl, $C_2$-$C_6$ alkenyl, $C_1$-$C_5$ alkoxy, or C₁-C₆ phenylalkyl, wherein alkyl, cycloalkyl or alkenyl group can be substituted by a COOH residue
a residue of formula SO₂R4 wherein R4 is C₁-C₂ alkyl, C₃-C₆ cycloalkyl, C₁-C₃ haloalkyl.
Preferably, in these compounds X is OH.

Among the above compounds, particularly preferred are also compounds of said formula (I) or pharmaceutically acceptable salts thereof, wherein
R1 is hydrogen;
R2 is hydrogen or linear C₁-C₄ alkyl, preferably it is hydrogen;
Y is a heteroatom selected from S, O and N; preferably it is S;
Z is selected from halogen, linear or branched C₁-C₄ alkyl, C₂-C₄ alkenyl, C₂-C₄ alkynyl, C₁-C₄ alkoxy, hydroxyl, carboxyl, C₁-C₄ acyloxy, phenoxy, cyano, nitro, amino, C₁-C₄ acylamino, halo C₁-C₃ alkyl, halo C₁-C₃ alkoxy, benzoyl, linear or branched C₁-C₈ alkanesulfonate, linear or branched C₁-C₈ alkanesulfonamides, linear or branched C₁-C₈ alkylsulfonylmethyl; preferably it is selected from trifluoromethyl;
X is OH or a residue of formula NHR₃; wherein R₃ is selected from
hydrogen, hydroxyl, linear or branched C₁-C₆ alkyl, C₃-C₆ cycloalkyl, C₂-C₆ alkenyl, C₁-C₅ alkoxy, or C₁-C₆ phenylalkyl, wherein alkyl, cycloalkyl or alkenyl group can be substituted by a COOH residue
a residue of formula SO₂R4 wherein R4 is C₁-C₂ alkyl, C₃-C₆ cycloalkyl, C₁-C₃ haloalkyl. More preferably X is NH₂.
Preferably, in the above compounds X is OH.

Among the above compounds, particularly preferred are also compounds of said formula (I) or pharmaceutically acceptable salts thereof, wherein:
R1 is hydrogen or CH₃;
R2 is hydrogen or linear C₁-C₄ alkyl, preferably it is hydrogen;
Y is a heteroatom selected from S, O and N; preferably it is S;
Z is selected from linear or branched C₁-C₄ alkyl, linear or branched C₁-C₄ alkoxy, halo C₁-C₃ alkyl and halo C₁-C₃ alkoxy; preferably it is selected from methyl, methoxy, trifluoromethoxy, trifluoromethyl, more preferably it is trifluoromethyl;
X is OH;

Among the above compounds, particularly preferred are also compounds of said formula (I) or pharmaceutically acceptable salts thereof, wherein:
R1 is CH₃;
R2 is hydrogen or linear C₁-C₄ alkyl, preferably it is hydrogen.
Y is a heteroatom selected from S, O and N; preferably it is S.
Z is selected from linear or branched C₁-C₄ alkyl, linear or branched C₁-C₄ alkoxy, halo C₁-C₃ alkyl and halo C₁-C₃ alkoxy; preferably it is selected from methyl, methoxy, trifluoromethoxy, trifluoromethyl, more preferably it is trifluoromethyl.

Among the above compounds, particularly preferred are also compounds of said formula (I) or pharmaceutically acceptable salts thereof, wherein
R1 is hydrogen;
X is OH;
R2 is hydrogen or linear C₁-C₄ alkyl, preferably it is hydrogen;
Y is a heteroatom selected from S, O and N; preferably it is S;
Z is selected from linear or branched C₁-C₄ alkyl, linear or branched C₁-C₄ alkoxy, halo C₁-C₃ alkyl and halo C₁-C₃ alkoxy; preferably it is trifluoromethyl.

Preferably, in all of the above compounds of formula (I) wherein R1 is hydrogen.

The chiral carbon atom of the phenylpropionic group is in the S configuration. Particularly preferred are compounds of formula (I) according to the invention selected from 2-methyl-2-(4-{[4-(trifluoromethyl)-1,3-thiazol-2-yl] amino} phenyl)propanoic acid (herein indicated also as DF2726Y) and pharmaceutically acceptable salts thereof, preferably its sodium salt (herein indicated also as DF2726A) and 2-(4-{[4-(trifluoromethyl)-1,3-thiazol-2-yl] amino}phenyl)propanoic acid and pharmaceutically acceptable salts thereof, preferably (2S)-2-(4-{[4-(trifluoromethyl)-1,3-thiazol-2-yl] amino} phenyl) propanoic acid (also known as DF2755Y) and its sodium salt, also known as DF2755A.

Compounds of formula (I) are disclosed in WO2010/031835, which also discloses their method of synthesis, their activity as IL-8 inhibitors as well as their use in the treatment of IL-8 dependent pathologies such as transient cerebral ischemia, bullous pemphigoid, rheumatoid arthritis, idiopathic fibrosis, glomerulonephritis and damages caused by ischemia and reperfusion.

Among the above IL-8 inhibitors, said 2-phenyl-propionic acid derivative is preferably a compound of formula (II):

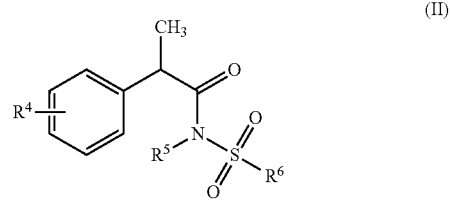

(II)

or a pharmaceutically acceptable salt thereof,
wherein
R⁴ is linear or branched C₁-C₆ alkyl, benzoyl, phenoxy, trifluoromethanesulfonyloxy; preferably it is selected from benzoyl, isobutyl and trifluoromethanesulfonyloxy. Also, according to a preferred embodiment R⁴ is in position 3 or 4 on the phenyl ring, more preferably it is 3-benzoyl, 4-isobutyl or 4-trifluoromethanesulfonyloxy.
R⁵ is H or linear or branched C₁-C₃ alkyl, preferably it is H.
R⁶ is linear or branched C₁-C₆ alkyl or trifluoromethyl; preferably, it is a linear or branched C₁-C₆ alkyl, more preferably it is CH₃.

Among the above compounds, preferred are compounds of formula (II) or a pharmaceutically acceptable salts thereof, wherein:
R⁴ is C₁-C₆ alkyl or benzoyl; preferably it is in positions 3 and 4, more preferably, it is 3-benzoyl or 4-isobutyl.
R⁵ is H or linear or branched C₁-C₃ alkyl, preferably it is H,
R⁶ is linear or branched C₁-C₆ alkyl or trifluormethyl; preferably it is a linear or branched C₁-C₆ alkyl, more preferably it is CH₃.

Among the above compounds, preferred are compounds of formula II or a pharmaceutically acceptable salts thereof, wherein:

R⁴ is trifluoromethanesulfonyloxy, preferably 4-trifluoromethanesulfonyloxy,

R⁵ is H or linear or branched $C_1$-$C_3$ alkyl, preferably it is H,

R⁶ is linear or branched $C_1$-$C_6$ alkyl or trifluormethyl; preferably it is a linear or branched $C_1$-$C_{16}$ alkyl, more preferably it is $CH_3$.

Among the above compounds, also preferred are compounds of formula (III):

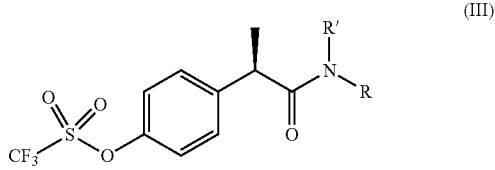

(III)

or a pharmaceutically acceptable salts thereof, wherein

R' is hydrogen;

R is a residue of formula $SO_2Ra$ wherein Ra is linear or branched $C_1$-$C_4$ alkyl or halo $C_1$-$C_3$ alkyl, preferably it is $CH_3$. Preferably, in the above compound of formula (II) or (III), the chiral carbon atom of the phenylpropionic group is in the R configuration.

Particularly preferred compounds of formula (II) according to the invention are selected from R-(-)-2-(4-isobutylphenyl)propionyl methansulfonamide (also known as Reparixin) and pharmaceutically acceptable salts thereof. Preferably, said compound is the lysine in situ salt of R(-)-2-(4-isobutylphenyl)propionyl methansulfonamide (herein indicated also as DF1681B). Further particularly preferred compounds of formula (II) or (III) according to the invention are 2-(4-trifluoromethanesulfonyloxy)phenyl]-N-methanesulfonyl propionamide and pharmaceutically salts thereof, preferably its sodium salt preferably R(-)-2-(4-trifluoromethanesulfonyloxy)phenyl]-N-methanesulfonyl propionamide (also known as DF2156Y) and its sodium salt (also known as Ladarixin or DF2156A).

IL-8 inhibitors of formula (II) and (III) are disclosed in WO0024710 and WO2005/090295, that also disclose their method of synthesis, their activity as IL-8 inhibitors as well as their use as inhibitors of neutrophils chemotaxis and degranulation induced by IL-8 and in the treatment of IL-8 dependent pathologies such as psoriasis, ulcerative colitis, melanoma, chronic obstructive pulmonary diseases (COPD), bullous pemphigoid, rheumatoid arthritis, idiopathic fibrosis, glomerulonephritis and damages caused by ischemia and reperfusion.

The chemotherapy-induced peripheral neuropathy according to the invention may be that induced by any chemotherapeutic agent having neurotoxic side effects. Preferably, said chemotherapeutic agent is selected from platinum-based drugs, taxanes, epothilones, plant alkaloids, thalidomide, lenalidomide and pomalidomide, carfilzomib, bortezomib and eribulin. More preferably, said chemotherapeutic agent is selected from cisplatin, carboplatin, oxaliplatin, paclitaxel, cabazitaxel, docetaxel, ixabepilone, vinblastine, vincristine, vinorelbine, etoposide, thalidomide, lenalidomide, pomalidomide, carfilzomib, bortezomib and eribulin. According to a preferred embodiment, the chemotherapy-induced peripheral neuropathy is that induced by a taxane, more preferably by paclitaxel.

EXAMPLES

Methods

Model of Induction of Neuropathy by Paclitaxel or Oxaliplatin

Male Wistar rats (200-250 g, Harlan Italy) were housed in a room with controlled temperature (22±1° C.), humidity (60±10%) and light (12 h per day); food and water were available ad libitum.

The rats received:
1—four once a day intraperitoneal (i.p.) injections of either paclitaxel (Tocris, Italy) (2 mg/kg/day i.p.; cumulative dose of 8 mg/kg i.p.) or vehicle (saline, 1 ml/kg/day i.p.), administered on alternate days (days 0, 2, 4, and 6), as described in Polomano et al, Pain 2001, 94:293-294. Behavioral testing was performed prior to paclitaxel/vehicle administration (day-1), and again on days 5-7-10-14 following paclitaxel/vehicle injection; or
2—oxaliplatin (2.4 mg/kg) dissolved in 5% glucose solution which was administered intraperitoneally (i.p.) at a volume of 0.5 mL/rat, for 5 consecutive days every week for 3 weeks, as described in Cavaletti et al., Eur. J. Cancer, 2001 37, 2457-63. Behavioral testing was performed before oxaliplatin/vehicle administration (day-1), and at again on day 3-5-7-10-14-21 day following oxaliplatin/vehicle injection.

Drug Treatment in the Above Models

1. Administration of DF2726A and DF1681B in Paclitaxel Model

In two separate studies, (2-methyl-2-(4-{[4-(trifluoromethyl)-1,3-thiazol-2-yl]amino} phenyl)propanoic acid sodium salt (herein indicated also as DF2726A) or R-(-)-2-(4-isobutylphenyl)propionyl methanesulfonamide (Reparixin, DF1681Y) dissolved in aqueous solution of lysine to form the in situ salt (herein indicated as DF1681B) were administered as described below.

DF2726A (30 mg/kg) (5 mg/1 ml, 0.5 ml/os/rat) was dissolved in 10% SOLUTOL-HS15 and N-methylpyrrolidone (NMP) (SOLUTOL:NMP 2:1 w/v) and 90% PBS 1x, and was administered once a day from day -3 up to day 11 after paclitaxel administration. Anti-allodynic effects were assessed on day 5, 7, 10 and 14 after paclitaxel administration. Control animals received vehicle (10% SOLUTOL-NMP 2:1 w/v and PBS, 5 mg/1 ml; 0.5 ml/os/rat).

DF1681B was administered by continuous subcutaneous infusion using the ALZET osmotic pumps Model 2ML2 (Charles River). In details, DF1681B (9.37 g) was dissolved in sterile saline (25 ml) at a concentration of 375 mg/ml and vortexed for 10 min. Osmotic pumps were implanted under anesthesia (100 mg/kg ketamine and 10 mg/kg xylazine i.p.) through a surgical incision between the scapulae. Pumps were implanted 3 days before first paclitaxel injection (day-3). Drug delivery was carried out continuously until day +11. Control animals received vehicle (sterile saline).

2. Administration of DF2726A and DF1681B in Oxaliplatin Model

In two separate studies, 2-methyl-2-(4-{[4-(trifluoromethyl)-1,3-thiazol-2-yl]amino} phenyl)propanoic acid sodium salt (herein indicated also as DF2726A) or R-(-)-

2-(4-isobutylphenyl)propionyl methanesulfonamide (reparixin, DF1681Y) dissolved in aqueous solution of lysine to form the in situ salt (herein indicated as DF1681B) were administered as described below.

DF2726A (30 mg/kg/os) was dissolved in PBS and it was administrated, for 24 consecutive days starting 3 days before oxaliplatin administration and continuing for other 21 days after the first administration of oxaliplatin. During this period the compound was given 2 h after oxaliplatin treatment. Since DF2726A is a sodium salt it was dissolved at the concentration of 16 mg/ml, to reach the active drug dose of 30 mg/kg.

DF1681B was administered by continuous subcutaneous infusion using the ALZET osmotic pumps Model 2ML2 (Charles River). In order to obtain a rate of infusion of 8 mg/hr/kg as described by Cavalieri et al Int J Immunopathol Pharmacol, 2005, 18:475-86, DF1681B (9.37 g) was dissolved in sterile saline (25 ml) at a concentration of 375 mg/ml and vortexed for 10 min. Osmotic pumps were implanted under anesthesia (100 mg/kg ketamine and 10 mg/kg xylazine i.p.). Pumps were prepared according to Alzet instructions sheet. Briefly, pumps were filled with 2 ml of DF1681B solution or vehicle using sterile syringe. Finally, pumps were kept in water bath overnight in stove at 37° C.

The osmotic pump (Alzet model 2ML2; Charles River) was inserted through a surgical incision made on the back. Briefly, a small incision was made in the skin between the scapulae and a pocket was formed by spreading apart the subcutaneous connective tissues, finally the incisions were sutured and closed with sutures. Pumps were implanted 3 days before oxaliplatin injection (day −3) and replaced with new ones at day 14 after implantation.

Evaluation of Mechanical Allodynia

To assess the development of mechanical allodynia, sensitivity to tactile stimulation was measured using the Dynamic Plantar Aesthesiometer (DPA, Ugo Basile, Italy). Animals were placed in a chamber with a mesh metal floor covered by a plastic dome that enabled the animal to walk freely, but not to jump. The mechanical stimulus were then delivered in the mid-plantar skin of the hind paw. The cut-off was fixed at 50 g. Testing was performed on both paws before (day −1) and then on days 5, 7, 10 and 14 after paclitaxel/vehicle administration or on days 0, 3, 5, 7, 10, 14 and 21 after oxalipaltin/vehicle administration.

Evaluation of Cold Allodynia

Cold sensitivity was measured as the number of foot withdrawal responses after application of acetone to the dorsal surface of the paw (2). A drop of acetone was applied to the dorsal surface of paws with a syringe connected to a thin polyethylene tube while the rats was standing on a metal mesh. A brisk foot withdrawal response, after the spread of acetone over the dorsal surface of the paw, was considered as a sign of cold allodynia. Cold responses were measured on both paws before (day −1) and, then on 5, 7, 10 and 14 days after paclitaxel/vehicle administration or on days 0, 5, 7, 10, 14 and 21 after oxalipaltin/vehicle administration.

Statistical Analysis

All data were presented as the mean±SEM. The significance of differences between groups was determined by two-way analyses of variance (ANOVA) followed by Bonferroni post hoc tests for multiple comparisons. The level of significance was set at $P<0.05$.

Example 1

Effect of DF2726A in Paclitaxel-Induced Mechanical and Cold Allodynia

Mechanical and cold allodynia were evaluated in three groups of animals: SHAM, which did not receive paclitaxel nor any other treatment, Control, which received paclitaxel and vehicle, and DF2726A-treated, which received paclitaxel and DF2726A. Administration of treatments was carried out according to the protocol described in Methods.

Figure 2:
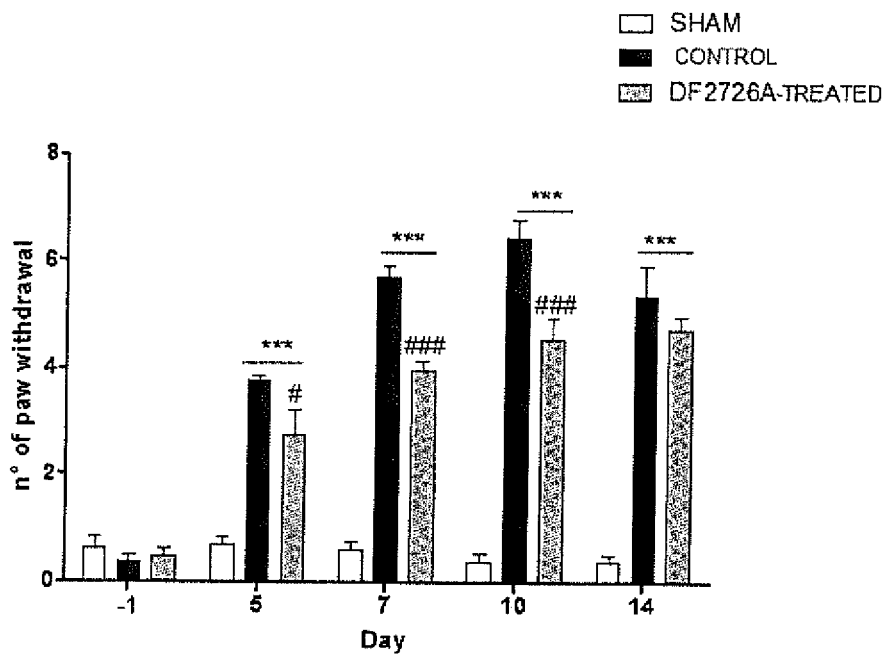
FIG. 2 represents the number of paw withdrawal, indicating the induction of allodynia induced by cold stimuli, measured as the number of foot withdrawal responses after application of acetone to the dorsal surface of the paw in an interval of 5 minutes evaluated in animals not subjected to any treatment with paclitaxel and/or vehicle/drug (Sham), treated with paclitaxel and vehicle (Control) or treated with paclitaxel and DF2726A (DF2726A-TREATED) before (day-1) and after (days 5, 7, 10, 14) paclitaxel administration in Control and DF2726A groups. Data are shown as mean±SEM of 10 animals per group. *** represents P<0.001 vs sham group; ### represents P<0.001 and # represents P<0.05 vs Control group.

Following paclitaxel administration animals in both Control and DF2726A-treated groups showed an evident mechanical and cold allodynia as compared to sham rats (FIG. 1 and FIG. 2).

In particular, in the Control group, in the Dynamic Plantar Aesthesiometer test, paw withdrawal threshold resulted significantly reduced at day 5, 7, 10 and 14, evidence of the onset of neuropathy (FIG. 1, black columns).

In the same group, in the cold allodynia test, the numbers of paw withdrawal threshold resulted significantly increased at days 5, 7, 10 and 14, evidencing the onset of neuropathy (FIG. 2, black columns).

Animals chronically treated with DF2726A (DF2726A-treated group) showed a significant reduction of mechanical allodynia at days 5 ($P<0.05$), 7 ($P<0.001$), and 10 ($P<0.001$) compared with animals treated with vehicle. No additional significant antiallodynic effect was measured on day 14 (FIG. 1).

Similarly, animals in the DF2726A-treated group showed a significant reduction of cold allodynia at days 5 ($P<0.05$), 7 ($P<0.001$), and 10 ($P<0.001$) compared with animals treated with vehicle. No additional antiallodynic effect was measured on day 14 (FIG. 2).

The obtained results clearly show that chronic oral administration of DF2726A for 14 days (from day −3 up to day 11) leads to a significant reduction of mechanical and cold allodynia at 5, 7 and 10 days after paclitaxel administration.

From day +12 up to day +14 following paclitaxel administration, rats did not received pharmacological treatment. As reported in FIGS. 1 and 2, on day 14 no additional antiallodynic effect was observed in the DF2726A-treated group, confirming that the antiallodynic activity is directly correlated with the administration of the compound.

Example 2

Effect of DF1681B in Paclitaxel-Induced Mechanical and Cold Allodynia

Mechanical and cold allodynia were evaluated in three groups of animals: Sham, which did not receive paclitaxel nor any other treatment, Control, which received paclitaxel and vehicle and DF1681B-treated, which received Paclitaxel and DF1681B. Administration of treatments was carried out according to the protocol described in Methods.

Figure 3:
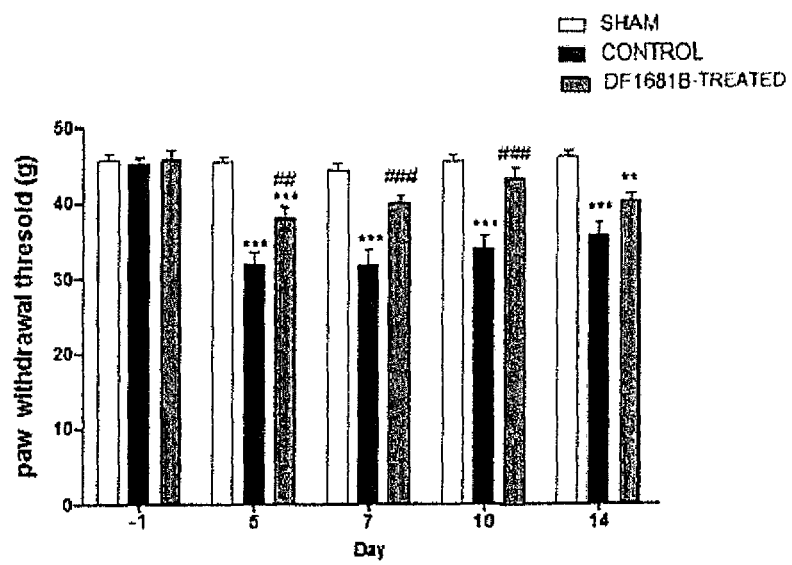
FIG. 3 represents the paw withdrawal threshold, indicating the induction of allodynia by mechanical stimuli, measured as measured as grams (g), in animals not subjected to any treatment with paclitaxel and/or vehicle/drug (Sham), treated with paclitaxel and vehicle (Control) or with paclitaxel and DF1681B (DF1681B-TREATED), before (day-1), or after (days 5, 7, 10, 14) paclitaxel administration in vehicle and drug-treated groups. Data are shown as mean±SEM of 10 animals per group. * represents P<0.001 vs sham group and  represents P<0.01 vs sham group; ### represents P<0.01 vs Control group and ## represents P<0.01 vs Control group.
Figure 4:
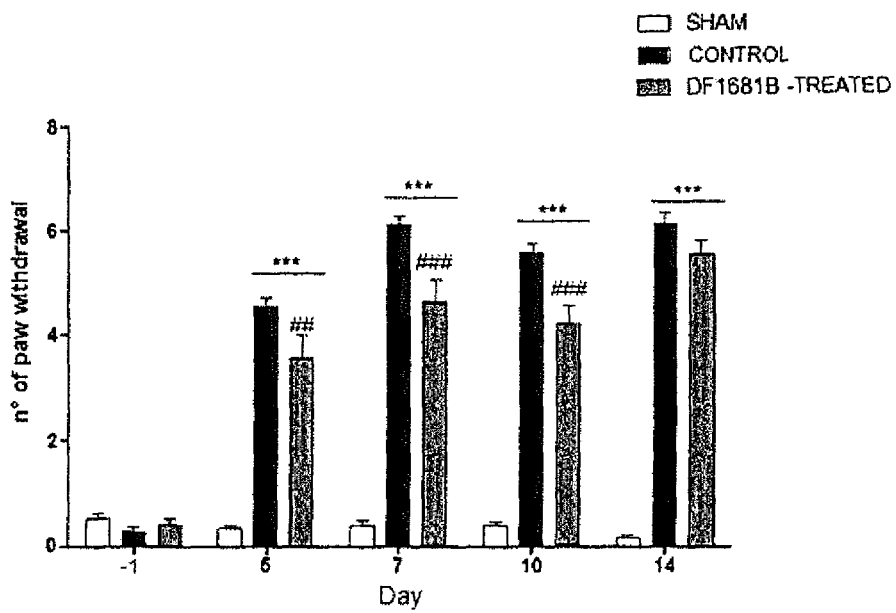
FIG. 4 represents the number of paw withdrawal, indicating the induction of allodynia induced by cold stimuli, measured as the number of foot withdrawal responses after application of acetone to the dorsal surface of the paw in an interval of 5 minutes evaluated in animals not subjected to any treatment with paclitaxel and/or vehicle/drug (Sham), treated with paclitaxel and vehicle (Control) or treated with paclitaxel and DF1681B (DF1681B-TREATED) before (day-1), or after (days 5, 7, 10, 14) paclitaxel administration in vehicle and drug-treated groups. Data are shown as mean±SEM of 10 animals per group, *** represents P<0.001 vs sham group; ### represents P<0.001 and ## represents P<0.01 vs Control group.

Following paclitaxel administration animals in both Control and DF1681B-treated groups showed an evident mechanical and cold allodynia as compared to Sham rats (FIGS. 3 and 4). In particular, in the Control group, in the DPA test, paw withdrawal threshold, resulted significantly reduced at day 5, 7, 10 and 14, evidence of neuropathy (FIG. 3).

Animals treated with DF1681B showed a significant reduction of mechanical allodynia at days 5 (P<0.01), 7 (P<0.001) and 10 (P<0.001) compared to animals treated with vehicle. No additional antiallodynic effect was measured on day 14 (FIG. 4). In cold allodynia experiments, in the Control group, the numbers of paw withdrawal threshold resulted significantly increased at days 5, 7, 10 and 14, evidence of neuropathy (FIG. 3). Animals treated with DF1681B showed a significant reduction of cold allodynia at days 5 (P<0.01), 7 (P<0.001), and 10 (P<0.001) compared to animals treated with vehicle. No additional antiallodynic effect was measured on day 14 (FIG. 4). The obtained results clearly show that DF1681B leads to a significant reduction of mechanical and cold allodynia at 5, 7, and 10 days after paclitaxel administration. Implantation of pumps on day −3 before paclitaxel produces a significant activity up to 10 day. On day 14, three days after the interruption of DF1681B administration, no effect was observed confirming that the antiallodynic activity is directly correlated with the delivery of the compound.

Example 3

Effect of DF1681B in Oxaliplatin-Induced Mechanical and Cold Allodynia

Mechanical and cold allodynia were evaluated in three groups of animals: Sham, which did not receive oxaliplatin nor any other treatment, Control, which received oxaliplatin and vehicle, and DF1681B-treated, which received oxaliplatin and DF1681B. Administration of treatments was carried out according to the protocol described in Methods.

Figure 5:
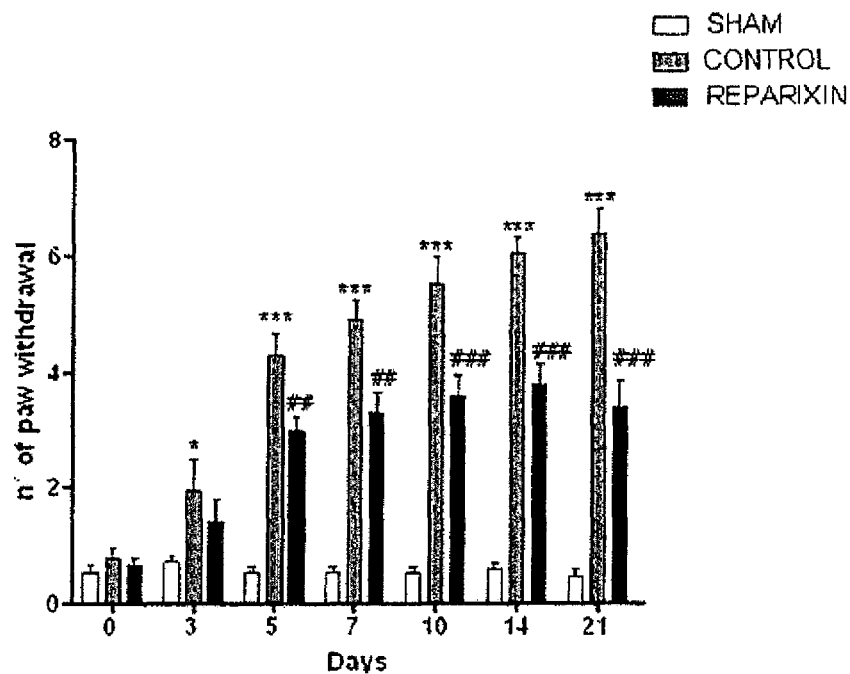
FIGS. 5 and 6 represent the effect of reparixin dissolved in aqueous solution of lysine to form the in situ salt (DF1681B) on oxaliplatin-induced allodynia. Cold (FIG. 5) and mechanical (FIG. 6) allodynia were evaluated on days 0, 3, 5, 7, 10, 14, 21. Data are shown as mean±SEM of 5-10 animals per group. * represents P<0.001,  represents P<0.01 and * represents P<0.05 vs sham group; ### represents P<0.001, and ## represents P<0.01 vs control group.

In cold allodynia experiments, animals treated with vehicle showed a number of paw withdrawal significantly increased at all experimental time-points (3, 5, 7, 10, 14, 21 day) due to neuropathy (FIG. 5), DF1681B did not show antiallodynic effect at day 3 (FIG. 5), while at days 5, 7, 10, 14, 21, it showed a significant reduction of cold allodynia (FIG. 5).

Figure 6:
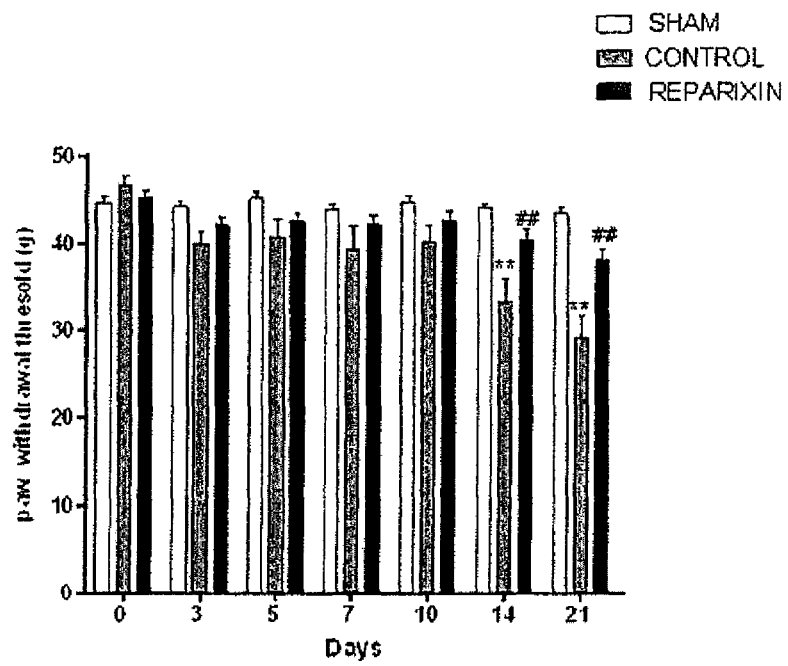

In mechanical allodynia experiments, paw withdrawal threshold resulted significantly reduced only at day 14 and 21, (FIG. 6); at these days DF1681B showed a significant antiallodynic effect (FIG. 6).

Example 4

Effect of DF2726A in Oxaliplatin-Induced Mechanical and Cold Allodynia

Mechanical and cold allodynia were valuated in three groups of animals: Sham, which did not receive oxaliplatin nor any other treatment, Control, which received oxaliplatin and vehicle, and DF2726A-treated, which received oxaliplatin and DF2726A. Administration of treatment drugs was carried out according to the protocol described in Methods above.

Figure 7:
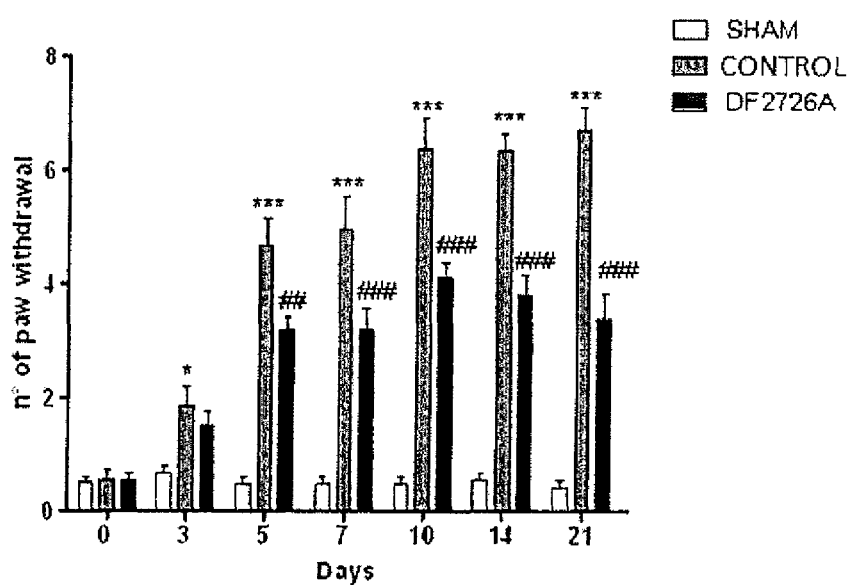
FIGS. 7 and 8 represent the effect of oral DF2726A administration on oxaliplatin-induced allodynia. Cold (FIG. 7) and mechanical (FIG. 8) allodynia were evaluated on days 0, 3, 5, 7, 10, 14, 21, one hour after oral administration. Data are shown as mean±SEM of 5-10 animals per group. * represents P<0.001,  represents P<0.01 and * represents P<0.05 vs sham group; ### represents P<0.001, ## represents P<0.01, and # represents P<0.05 vs control group.
Figure 8:
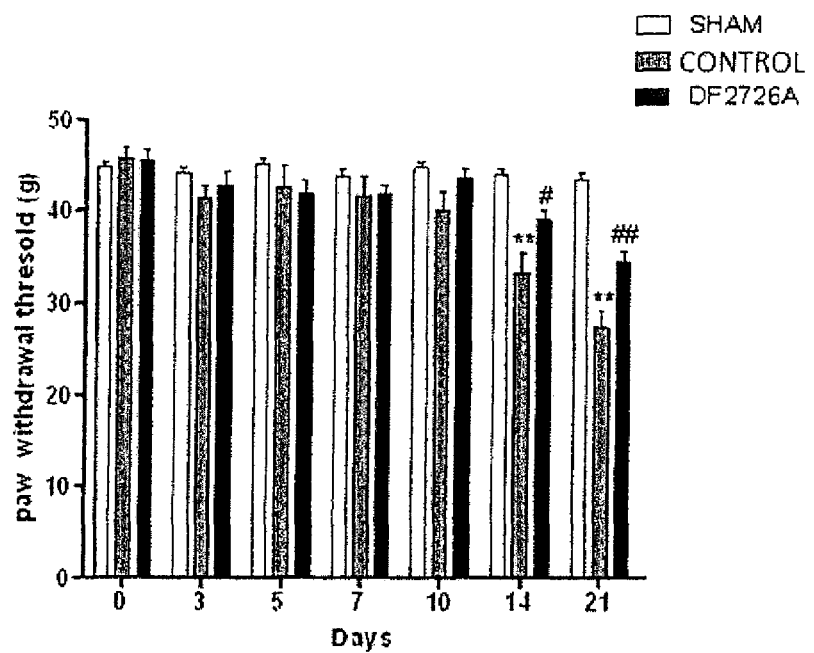

In cold allodynia experiments, animals treated with vehicle showed a number of paw withdrawal significantly increased at all experimental time-points (3, 5, 7, 10, 14, 21 days) due to neuropathy (FIG. 7). DF2726A did not show antiallodynic effect at day 3, while at days 5, 7, 10, 14, 21, it showed a significant reduction of cold allodynia (FIG. 7). In mechanical allodynia experiments, paw withdrawal threshold resulted significantly reduced only at days 14 and 21, (FIG. 8); DF2726A at these days, showed a significant antiallodynic effect (FIG. 8).

Example 5

Effect of Reparixin in Paclitaxel-Induced Cytoskeleton Modifications

In this study, the effects of paclitaxel, administered alone or in combination with reparixin (DF1681Y; R-(−)-2-(4-isobutylphenyl)propionyl methanesulfonamide) dissolved in aqueous solution of lysine to form the in situ salt, on the cytoskeleton components and organization was performed. As experimental model, a F-11 cell line, a fusion product of mouse neuroblastoma cell line N18TG-2 cells with embryonic rat dorsal root ganglia sensory neurons, was used. These cells were selected because of the presence of neuronal markers and properties that are unique to the parental rat sensory neurons.

Cell Culture and Treatments

F11 (ECACC, Salisbury, UK) cells were cultivated DMEM (Euroclone, MI, Italy) medium supplemented with 10% FBS, USA origin, (Sigma-Aldrich St. Louis, CO, USA), 1% penicillin/streptomycin (Euroclone) and 1% glutamine (Euroclone). After, cells were differentiated with mouse NGF (mNGF) dissolved in DMEM with 1% penicillin/streptomycin and 1% glutamine (FBS free) at the final concentration 50 ng/ml. Medium was replaced every 3 days until complete differentiation, occurred after 7 days. Neurons were not treated (controls) or treated for 24 hours with reparixin [10 μM final concentration], paclitaxel (Sigma-Aldrich) [10 nM final concentration] and the combination of the two molecules.

Immunofluorescence

Cells were fixed in paraformaldehyde 4% in PBS for 20 min at RT and permeabilized in methanol for 5 min at −20° C. Cells were then blocked with PBS containing 4% BSA for 30 min and incubated with primary antibodies diluted in the blocking solution overnight at 4° C.: rabbit β-tubulin (Abcam, Cambridge, UK) 1:500; mouse α-tubulin (Abcam) 1:200 and mouse α-tubulin acetylated (Abcam) 1:1000. Cells were then rinsed in PBS several times before incubation with secondary antibodies, goat anti rabbit conjugated with Alexafluor 633 (1:2000), and goat anti mouse conjugated with Alexafluor 488 (1:2000), (Life Technologies, CA, USA) for 30 min at RT. After extensive washing coverslips were mounted with Vectashield mounting medium with DAPI (Vector Laboratories Burlingame, CA, USA) and then observed at confocal laser microscope.

Results

In control neurons probed for anti-acetylated α-tubulin (marker of stable microtubules) the acetylated tubulin appeared moderately present. The same marker was evaluated in paclitaxel-treated neurons. In agreement with the literature, paclitaxel increased acetylated α-tubulin, affecting microtubule dynamics and causing stabilization and maturation of the dendritic spines. In fact, the fluorescence intensity in neurites appears more intense and an increase of neurite diameter and cytoskeleton organization is apparent.

In the experiment using a combination of paclitaxel and reparixin, acetylated α-tubulin appears similar to the control, thus indicating that the presence of reparixin is able to counteract the paclitaxel effects that causes an increase of microtubules stability by increasing acetylated α-tubulin and neurite thickness. Cells were then assayed with anti-α-tubulin and anti-β-tubulin both in control and treated conditions and the double and single immunofluorescence was evaluated. When neurons were treated with paclitaxel, a decrease of the fluorescence intensity of β-tubulin was observed. Also in this experiment on α- and β-tubulin, the combination of paclitaxel with reparixin was able to counteract the effect of paclitaxel alone on dimer formation and cells appeared more similar to control cells.

The results demonstrate that inhibition of IL-8 is able to prevent the effect of chemotherapy on allodynia (both mechanical and cold) in rat models as well as to counteract the effects of paclitaxel on microtubules stability and cytoskeleton organization in a chimeric neuronal cell line.

A body of findings provide evidence that proinflammatory cytokines and chemokines are involved in the pathogenesis of acute and chronic peripheral pain [Wang X M et al, Cytokine 2012; 59:3-9; Ramesh G. 2014; Inflamm Cell Signal 1 (3)]. In response to chemotherapy-induced injury, macrophage infiltration leads to a subsequent production of a plethora of mediators among which proinflammatory cytokines (TNF-α, IL-1β, IL-6, IL-8) play essential roles in the initiation and progression of CIPN. Most notably, the chemokine IL-8 has been implicated in contributing directly to motor-neuron degeneration [De Paola M et al, Neuroimmunomodulation 2007; 14 (6):310-6].

With regards to the mechanisms of CIPN attenuation by IL-8 inhibitors, in vitro studies reveal that reparixin was able to counteract the effects on cytoskeleton components and organization induced by paclitaxel. In particular, the compound was able to abolish the induction of a-tubulin acetylation, a marker for microtubule stability and the increased neurite thickness induced by paclitaxel treatment, contributing to restore the physiological microtubules dynamics.

The invention claimed is:

1. A method of treating and/or preventing chemotherapy-induced neuropathy, wherein the chemotherapy-induced neuropathy is chemotherapy-induced peripheral neuropathy or chemotherapy-induced optic neuropathy and wherein the chemotherapy-induced neuropathy is induced by a chemotherapeutic agent selected from the group consisting of taxanes and platinum based drugs, in a subject in need thereof, comprising administration of an IL-8 inhibitor, wherein the IL-8 inhibitor is a compound of formula (II)

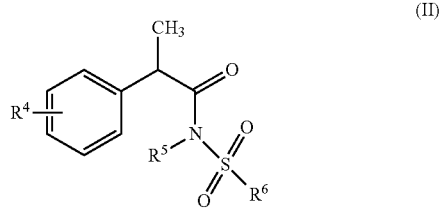

(II)

or a pharmaceutically acceptable salt thereof,
wherein:
R4 is linear or branched $C_1$-$C_6$ alkyl, benzoyl, phenoxy, or trifluoromethanesulfonyloxy;
$R^5$ is H or linear or branched $C_1$-$C_3$ alkyl;
$R^6$ is linear or branched $C_1$-$C_6$ alkyl or trifluoromethyl.

2. The method according to claim 1, wherein $R^4$ is 3-benzoyl, 4-isobutyl or 4-trifluoromethanesulfonyloxy.

3. The method according to claim 1, wherein $R^6$ is $CH_3$.

4. The method according to claim 1, which method comprises treating and/or preventing allodynia associated with chemotherapy-induced peripheral neuropathy.

5. The method according to claim 1, wherein the IL-8 inhibitor is an inhibitor of the activity of IL-8 mediated by the CXCR1 receptor.

6. The method according to claim 1, wherein the IL-8 inhibitor is an inhibitor of the activity of IL-8 mediated by both the CXCR1 and CXCR2 receptor.

7. The method according to claim 1, wherein the compound is R-(-)-2-(4-isobutylphenyl) propionyl methanesulfonamide or a pharmaceutically acceptable salt thereof.

8. The method according to claim 7, wherein the compound is in the form of its lysine in situ salt.

9. The method according to claim 1, wherein the chemotherapy-induced peripheral neuropathy is induced by a taxane.

10. The method according to claim 9, wherein the taxane is paclitaxel.

11. The method according to claim 1, wherein the chemotherapy-induced peripheral neuropathy is induced by a platinum based drug.

12. The method according to claim 11, wherein the platinum based drug is oxaliplatin.

13. A method of treating and/or preventing chemotherapy-induced neuropathy, wherein the chemotherapy-induced neuropathy is chemotherapy-induced peripheral neuropathy or chemotherapy-induced optic neuropathy and wherein the chemotherapy-induced neuropathy is induced by a chemotherapeutic agent selected from the group consisting of taxanes and platinum based drugs, in a subject in need thereof, comprising administration of an IL-8 inhibitor, wherein the IL-8 inhibitor is a compound of formula (III)

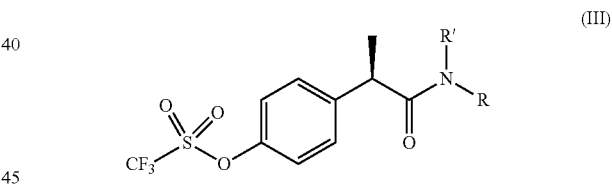

(III)

or a pharmaceutically acceptable salt thereof,
wherein
R' is hydrogen;
R is a residue of formula $SO_2Ra$ wherein Ra is linear or branched $C_1$-$C_4$ alkyl or halo $C_1$-$C_3$ alkyl.

14. The method according to claim 13, wherein the chiral carbon atom of the phenylpropionic group is in the R configuration.

15. The method according to claim 14, wherein the compound is R(-)-2-(4-trifluoromethanesulfonyloxy)phenyl]-N-methanesulfonyl propionamide or a pharmaceutically acceptable salt thereof.

16. The method according to claim 15, wherein the compound is in the form of its sodium salt.

* * * * *